US008694114B2

(12) United States Patent
Churchill (10) Patent No.: US 8,694,114 B2
(45) Date of Patent: Apr. 8, 2014

(54) SYSTEM AND METHOD FOR FINE-STRUCTURE PROCESSING FOR HEARING ASSISTANCE DEVICES

(75) Inventor: Tyler Hale Churchill, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/400,754

(22) Filed: Feb. 21, 2012

(65) Prior Publication Data

US 2013/0218236 A1 Aug. 22, 2013

(51) Int. Cl.
*A61N 1/00* (2006.01)
(52) U.S. Cl.
USPC .......................................................... 607/57
(58) Field of Classification Search
USPC .......................................................... 607/57
See application file for complete search history.

(56) References Cited

U.S. PATENT DOCUMENTS 6,594,525 B1   7/2003  Zierhofer
7,310,558 B2 * 12/2007 Van Hoesel ..................... 607/57

OTHER PUBLICATIONS

Chen, et al, Zerocrossing-Based Nonuniform Sampling to Deliver Low-Frequency Fine Structure Cue for Cochlear Implant, Digital Signal Processing, 2011, 21:427-432.
Smith, et al., Chimaeric Sounds Reveal Dichotomies in Auditory Perception, Nature, 2002, 416(6876):87-90.

* cited by examiner

*Primary Examiner* — Christopher D Koharski
*Assistant Examiner* — Nadia Ahmad
(74) *Attorney, Agent, or Firm* — Quarles & Brady, LLP (57) ABSTRACT

A hearing assistance device and method is presented. An electrode is configured to be disposed within a cochlea of a user. A processor is in communication with the electrode and is configured to stimulate the electrode. The processor is configured to receive an input audio signal, band-pass filter the input audio signal into a plurality of channel signals, apply a Hilbert transform to at least one of the plurality of channel signals to generate a transformed audio signal, and analyze the transformed audio signal to identify at least one positive-moving zero crossing of the transformed audio signal. Upon identifying the at least one positive-moving zero crossing of the transformed audio signal, the processor is configured to trigger an electric current pulse to be delivered to the electrode.

9 Claims, 8 Drawing Sheets

SYSTEM AND METHOD FOR FINE-STRUCTURE PROCESSING FOR HEARING ASSISTANCE DEVICES

STATEMENT REGARDING FEDERALLY SPONSORED RESEARCH OR DEVELOPMENT

This invention was made with government support under DC003083 awarded by the National Institutes of Health. The government has certain rights in the invention.

CROSS-REFERENCE TO RELATED APPLICATIONS

N/A

FIELD OF THE INVENTION

The invention relates to a system and method for signal processing in hearing assistance devices, such cochlear implants, and, more particularly, to a system and method for fine-structure processing for devices such as cochlear implants.

BACKGROUND OF THE INVENTION

Cochlear implants (CIs) are surgically-implanted prosthetic devices that can provide the profoundly deaf with sensations of sound. In normal hearing, incoming sound is frequency-analyzed by the inner ear's cochlea. High frequency sounds are picked out near the base of the cochlea while low frequency sounds resonate within the cochlea's apical region. Nerve cells disposed within those different regions detect the vibrations and then transmit corresponding nerve impulses to the brain where the impulses are perceived as sound.

In an attempt to replicate this place-frequency map in electric hearing, doctors implant electrodes at specific insertion depths in the cochlea. The electrodes are then activated by incoming sound energy, where sound waves of a particular frequency cause the activation of one or more electrodes positioned at a particular location or depth within the cochlea. When an electrode is activated, the electrode stimulates the nearby tissue with a number of electric current pulses.

The electric pulses are detected by surviving auditory nerve fibers near that region. The electric pulses are typically generated at a constant rate, resulting in a sensation of sound. The louder an incoming sound, the more current is delivered with each of these pulses. Different frequencies of incoming sound waves are reflected in the cochlear implant by stimulating electrodes at different depths within the inner ear.

While cochlear implants improve the quality of life for hundreds of thousands of people worldwide, electric hearing still lacks the resolving ability found in normal hearing. For example, users of cochlear implants have difficulty with pitch detection and sound source localization.

Electric hearing does not operate in the same manner as normal hearing. In normal hearing, the nerve firings that result from cochlear excitation by an incoming sound wave are timed in accordance with the shape of waveform of the incoming wave, a phenomenon called phase locking. As a result, the nerve firings are not strictly periodic because the shape of the incoming waveform is somewhat random. In contrast, the constant rates of conventional cochlear implant stimulation are strictly periodic and can lead to a process called adaptation, whereby the nervous system ignores the repetitive periodic signal. As a result, at least some of the stimulation signals are ignored by the nervous system, reducing information transfer. Exacerbating this condition, the electric pulses of cochlear implants induce "super" phase locking, removing the natural randomness of the timing of nerve firings. It is thought that these deleterious effects are partially responsible for the reduced ability of bilaterally-implanted cochlear implant listeners' to take advantage of binaural cues in comparison with listeners having two normally-functioning ears.

Listening in noisy environments is notoriously difficult for cochlear implant users. For example, many users of cochlear implants report substantial deterioration of speech perception in noisy environments. In fact, noisy or complex sound environments can be unpleasant for users of cochlear implants. These difficulties stem from the inability of cochlear implant users to segregate target sounds and background maskers. Contemporary cochlear implant processing does not preserve many of the physical attributes of sounds that make them unique, such as temporal fine structure.

Therefore, it would be desirable to have a system and method for assisting with sound reception and perception that extracts and presents temporal fine structure from acoustic signals, a feat not achieved by traditional hearing assistance devices, such as traditional cochlear implants.

SUMMARY

The invention relates to a system and method for signal processing in hearing assistance devices, such cochlear implants, and, more particularly, to a system and method for temporal fine-structure processing for devices such as cochlear implants.

In one implementation, the present invention is a cochlear implant, comprising an electrode configured to be disposed within a cochlea of a user, and a processor in communication with the electrode and configured to stimulate the electrode. The processor is configured to receive an input audio signal, band-pass filter the input audio signal into a plurality of channel signals, apply a Hilbert transform to at least one of the plurality of channel signals to generate a transformed audio signal, and analyze the transformed audio signal to identify at least one positive-moving zero crossing of the transformed audio signal. Upon identifying the at least one positive-moving zero crossing of the transformed audio signal, the processor is configured to trigger an electric current pulse to be delivered to the electrode.

In another implementation, the present invention is a method of generating a stimulating signal for a hearing assistance device. The method includes receiving an input audio signal, band-pass filtering the input audio signal into a plurality of channel signals, applying a Hilbert transform to at least one of the plurality of channel signals to generate a transformed audio signal, and analyzing the transformed audio signal to identify at least one positive-moving zero crossing of the transformed audio signal. Upon identifying the at least one positive-moving zero crossing of the transformed audio signal, the method includes triggering an electric current pulse to be delivered to an electrode.

In another implementation, the present invention is a method of generating a stimulating signal for a cochlear implant. The method includes receiving a signal, applying a Hilbert transform to the signal to generate a transformed signal, and analyzing the transformed signal to identify at least one positive-moving zero crossing of the transformed signal. Upon identifying the at least one positive-moving zero crossing of the transformed signal, the method includes triggering an electric current pulse to be delivered to an electrode.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Some of the functional units described in this specification have been labeled as modules in order to more particularly emphasize their implementation independence. For example, a module may be implemented in field programmable gate arrays, programmable array logic, programmable logic devices, or the like. Modules may also be implemented in software for execution by various types of processors.

Figure 3:
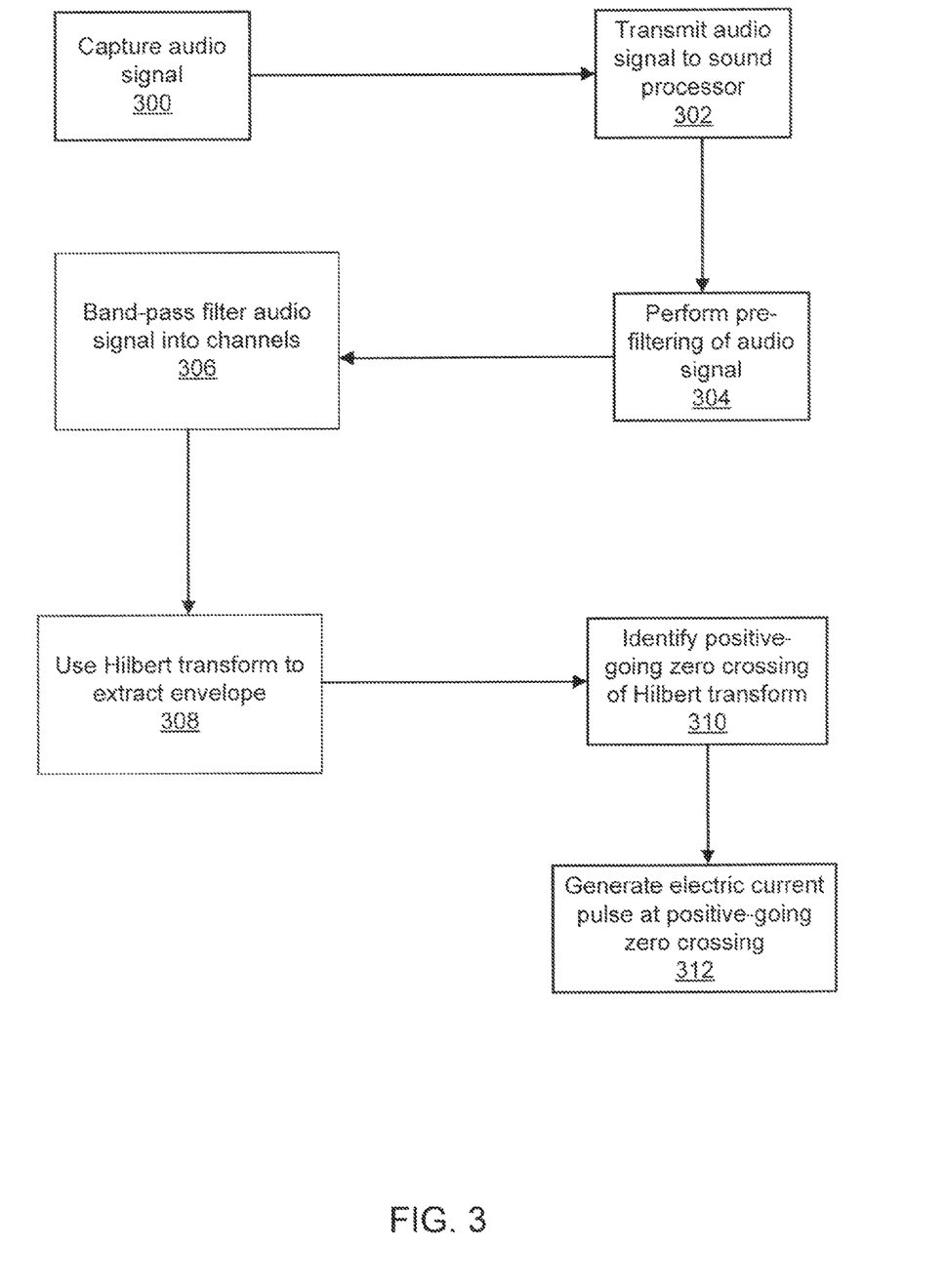
FIG. 3 is a flowchart illustrating an algorithm for encoding sound that may be executed by a sound processor of a cochlear implant in accordance with the present disclosure.

The schematic flow chart diagrams included are generally set forth as logical flow-chart diagrams (e.g., FIG. 3). As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood to not limit the scope of the method. Although various arrow types and line types may be employed in the flow-chart diagrams, they are understood to not limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The invention will be described as embodied in an apparatus and method for executing an algorithm to encode a stimulating signal based upon incoming sound waves for hearing assistance devices, which may include cochlear implants. Hereafter, reference is made to cochlear implants, but it is generally recognized that the present invention may be extended to other hearing assistance devices. The encoding is generally based on the physiological aspect of normal hearing that nerve firings generally occur at a certain phase of the acoustic waveform. As such, the present algorithm generates electrical stimulating pulses to be delivered to a cochlear implant where the pulses are timed to occur near the maxima of an input acoustic waveform.

Because these consecutive maxima are not strictly periodic, adaptation, one of the problems with conventional cochlear implants, is minimized allowing for improved use of both monaural and binaural cues. Furthermore, the algorithm results in a stimulating signal having low rates for low-frequency channels that are better used by cochlear implant users for rate discrimination. Improved rate discrimination allows the user to have improved pitch determination and interaural time difference discrimination. This improves the cochlear implant user's localization ability over that provided by traditional amplitude-modulated high-rate pulse train stimulating signals, especially when the pulse trains within the stimulating signal are non-periodic, as found in conventional devices.

Figure 1:
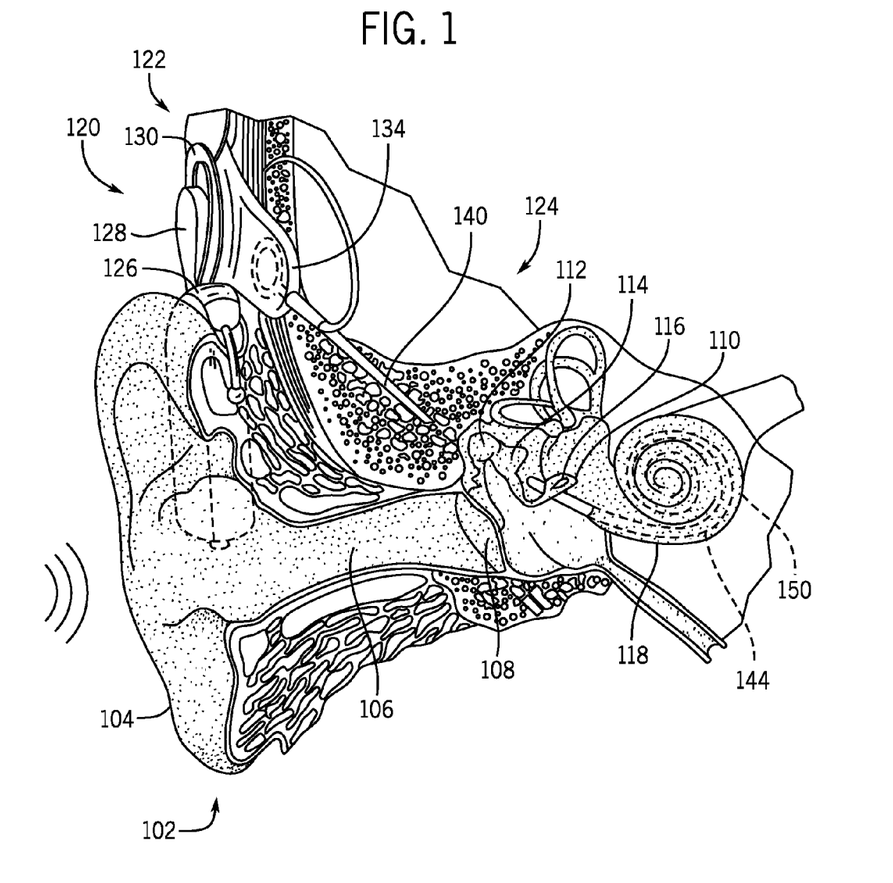
FIG. 1 is a view of an implanted cochlear implant that may be used to implement the present invention.

FIG. 1 is a view of an implanted cochlear implant 120 that may be used to implement the present invention, as described below. As shown in FIG. 1, the human ear includes outer ear 102. Outer ear 102 includes auricle 104. Extending away from auricle 104 is ear canal 106.

As an acoustic or sound wave impinges upon outer ear 102, auricle 104 collects the incoming sound wave and channels the sound wave into ear canal 106. The sound wave, after passing through ear canal 106 strikes tympanic membrane 108. The sound wave causes tympanic membrane 108 to vibrate. That vibration is then transferred to fenestra ovalis 110 through the three bones of the ear referred to as the malleus 112, the incus 114 and the stapes 116.

Bones 112, 114 and 116 of the ear serve to filter and amplify the incoming sound wave. The vibration of bones 112, 114 and 116 cause fenestra ovalis 110 to articulate, or vibrate. That vibration is detected by nerves attached to small hair cells lining the inside of the cochlear (element 118) and is ultimately perceived as sound.

In some individuals, a cochlear implant is used to directly stimulate the auditory nerves of the cochlea. FIG. 1 shows cochlear implant 120 comprising an external component assembly 122 that is directly or indirectly attached to the body of the user, and an internal component assembly 124 which is temporarily or permanently implanted in the user. External assembly 122 comprises several components to implement the functionality of the cochlear implant. The component include a plurality of audio sensors spatially arranged on external components 122 of cochlear implant 120 for detecting sound, as well as a sound processor.

Sound processor 126 of cochlear implant 120 generates coded stimulation control signals based upon an incoming sound wave that is detected by the audio sensors. The stimulation control signals represent the detected sound signals and are ultimately delivered to transmitter unit 128.

Transmitter unit 128 includes an external coil 130 and, preferably, a magnet (not shown) secured directly or indirectly within external coil 130. Transmitter unit 128 is configured to transmit the coded signals from sound processor 126 to internal components 124 of implant 120.

Internal components 124 comprise an internal receiver unit having an internal coil (not shown) that receives and transmits power and coded signals received from external assembly 122 to a stimulator unit 134 to apply the coded signal to cochlea 118 via an implanted electrode assembly 140. Electrode assembly 140 enters cochlea 118 and has one or more electrodes 150 positioned to be substantially aligned with portions of cochlea 118. Signals generated by the stimulator unit are typically applied by an array 144 of electrodes 150 to cochlea 118, thereby stimulating the auditory nerve.

Figure 2:
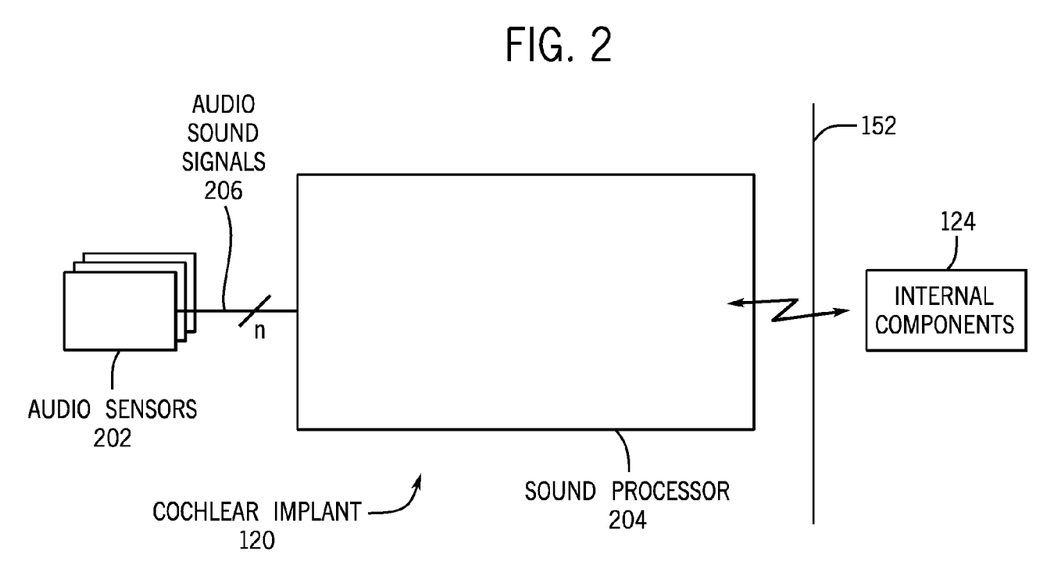
FIG. 2 is a block diagram showing functional components of the cochlear implant illustrated in FIG. 1.

FIG. 2 is a block diagram showing functional components of cochlear implant 120 illustrated in FIG. 1. Cochlear implant 120 comprises internal components 124 and external components 122 as described above with reference to FIG. 1. Audio sensors 202 are spatially-arranged in a plurality of external components of cochlear implant 120 to receive ambient sound. For example, an audio sensor may be located in one of the external components of the cochlear implant, while at least one other audio sensor is located elsewhere, such as in an external component other than the first external component. In certain embodiments, audio sensors 202 are further configured to deliver the sound sensed by the plurality of audio sensors to sound processor 204 as one or more received audio sound signals 206. In other implementations, cochlear implants may incorporate only a single audio sensor per external processor.

Sound processor 204 is configured to process sound received from one of more of audio sensor 202 and may modify the signal (e.g., by eliminating, canceling, filtering, or reduce noise or other unwanted aspects of the incoming audio signal). The filtered sound signal can then be converted into a stimulation control signal by sound processor 204. These coded stimulation control signals are then delivered to internal components 124 of cochlear implant 120.

In conventional cochlear implant systems, auditory nerve fibers are activated by a train of electric current pulses formed within a particular stimulation control signal that is delivered by the implanted electrodes at a constant rate. This constant-rate stimulation gives the user a sensation of sound. Generally, the louder an incoming sound, the more current is delivered with each of these pulses.

Unfortunately, this constant-rate stimulation can result in adaptation, where the nervous system ignores the repetitive periodic signal, reducing information transfer from the device to the user. Making this problem worse, the electric pulses of cochlear implants induce "super" phase locking, removing natural randomness of the timing of nerve firings. It is thought that these deleterious effects are partially responsible for bilaterally-implanted cochlear implant listeners' reduced ability to take advantage of binaural cues, compared with listeners with two normally-functioning ears. In normal hearing, the nerve firings that result from cochlear excitation by a sound are timed in accordance with the shape of waveform of the incoming signal, a phenomenon called phase locking.

In the present system, therefore, the sound processor of a cochlear implant is configured to generate a stimulation control signal that is arranged to include electrical pulses that are timed to occur at or substantially near the maxima of an input acoustic waveform. Because the consecutive maxima of the audio signal (and, consequently, the pulses of the stimulation control signal) are not strictly periodic, the problems associated with adaptation in conventional cochlear implant devices are minimized allowing for better use of both monaural and binaural cues. Additionally, the stimulation control signal created by the sound processor includes low pulse rates in channels corresponding to low frequencies, allowing for improved pitch determination and interaural time difference discrimination for localization ability. The amplitude of the delivered stimulation control signal pulses are modulated by envelope height of the input sound signal to encode loudness level fluctuations.

In another implementation of the present system, the pulses in the stimulation control signal for a given channel are triggered by positive-going zero-crossings of the angle of the Hilbert transform of the channel output audio signal, where the time domain signal waveform is near a maximum. In the case of high-frequency channels, a random-length refractory period may be imposed between pulses to keep rates below a maximum threshold value (e.g., 2000 pulses per second).

These processing schemes provide important cues (e.g., binaural timing cues) to the nervous system that are not accessible with current processing paradigms as they result in a stimulation control signal that encodes at least a portion of the temporal fine structure of the input audio signal. These schemes also provide improvements in pitch detection and sound source localization. As a result, the benefit of bilateral implantation can be significantly improved over unilateral implantation with the availability of localization cues.

Figure 4:
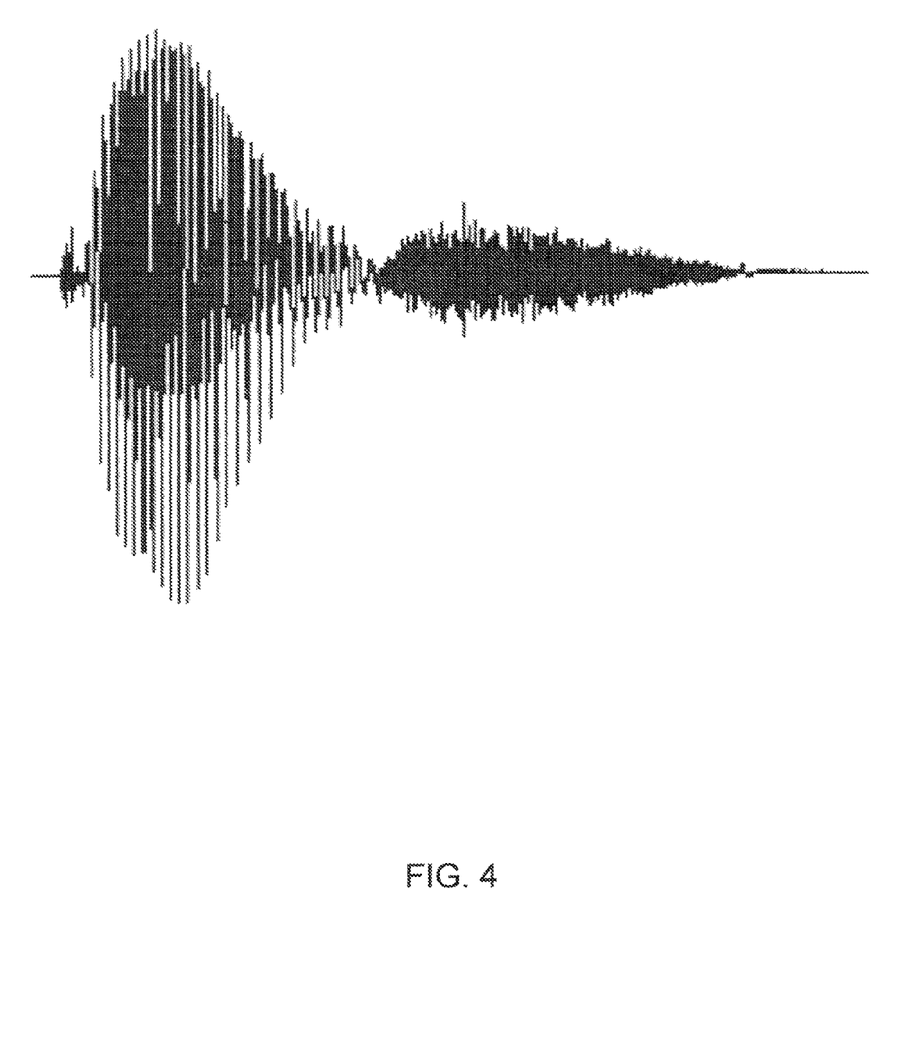
FIG. 4 is a graph showing a wave form of an example audio signal that may be captured by a cochlear implant in accordance with the present disclosure.

FIG. 3 is a flowchart illustrating an algorithm for encoding sound that may be executed by a sound processor of a cochlear implant in accordance with the present disclosure. The algorithm uses a Hilbert transform of channels of an input audio signal to generate an output stimulating control signal. In step 300 of the algorithm, an audio signal is captured by one or more audio sensor of a cochlear implant (e.g., cochlear implant 120 as shown in FIG. 1). The audio signal may be the sum of audio signals that are captured by more than one audio sensor (e.g., microphone) where the audio sensors are positioned about the ear of the cochlear implant user. Alternatively, the audio signal may be captured by a single audio sensor that is connected to the cochlear implant. FIG. 4 is a graph showing a wave form of an example audio signal that may be captured by a cochlear implant in accordance with the present disclosure.

Returning to FIG. 3, once captured, the audio signal is transmitted to a sound processor (e.g., sound processor 204 of FIG. 2) in step 302 for processing. The sound processor analyzes the incoming sound signal to generate an output stimulating control signal. The control signal is defined by a train of electric current pulses that are delivered through the cochlear implant into the user's ear, as described above.

Before generating the stimulating control signal, the sound processor may perform preliminary modifications of the input audio signal (e.g., by eliminating, canceling, filtering, or reduce noise or other unwanted aspects of the incoming audio signal) as shown in step 304. For example, the sound processor may exercise automatic gain control to adjust the gain for a given sound input level.

Figure 5:
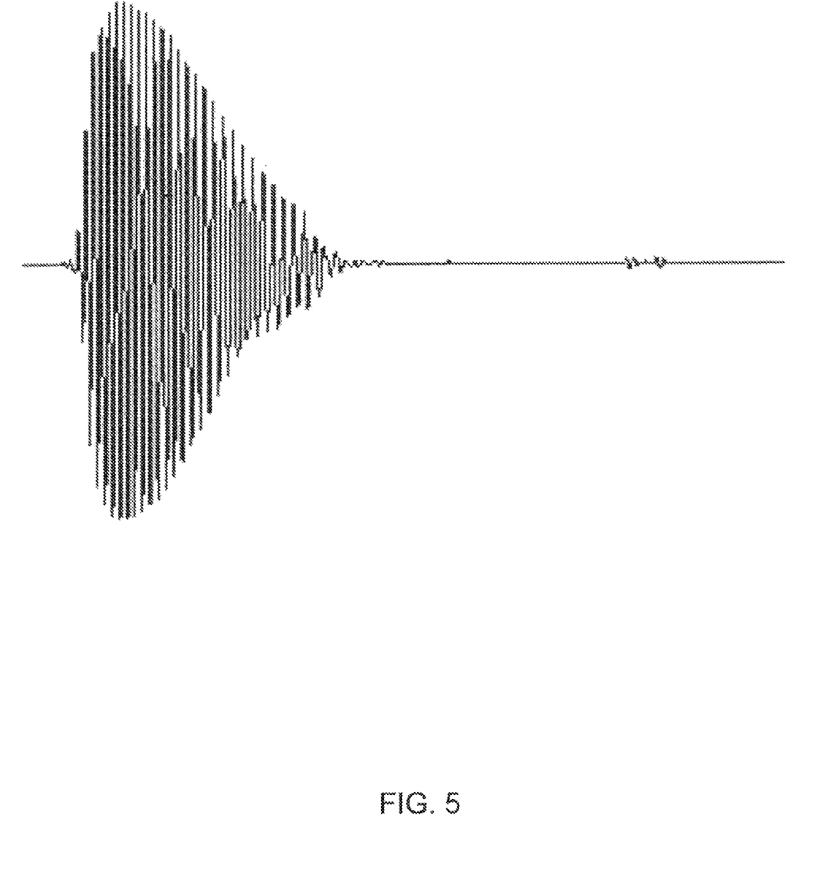
FIG. 5 is a graph showing a band-passed channel of the example audio signal shown in FIG. 4.

The incoming acoustic signal is then band-pass filtered into a number of channels in step 306, with each channel having a particular frequency range and corresponding to a single electrode within the cochlear implant. After the audio signal is filtered into channels by the sound processor, the sound processor analyzes the filtered audio signal of each channel to generate a stimulating control signal for each corresponding electrode. The amplitude modulation of the current pulses is determined by the envelope of the output of each channel's band-pass filter. FIG. 5 is a graph showing a band-passed channel of the example audio signal shown in FIG. 4.

Figure 6:
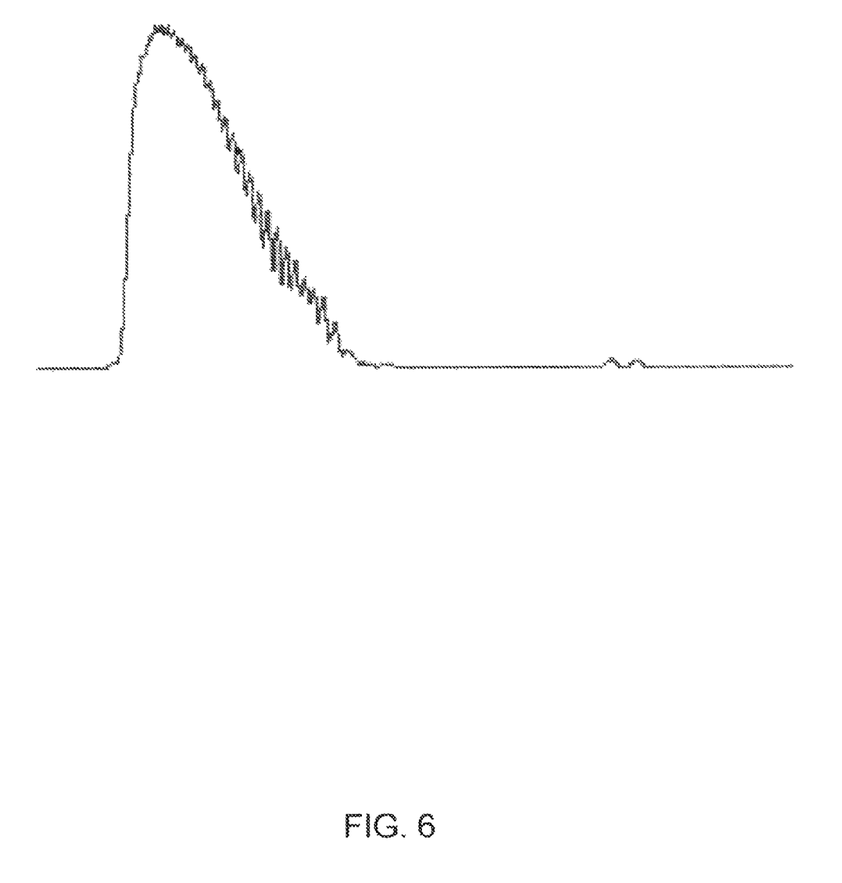
FIG. 6 is a graph showing the magnitude of the Hilbert transform of the band-pass filtered audio signal shown in FIG. 6.

In step 308, the envelope of the each channel's audio signal may be extracted by first taking the absolute value of the Hilbert transform of the signal. A Hilbert transform is a mathematical transform that can be used to factor a signal into the product of a slowly varying envelope and a rapidly varying fine time structure. The envelope of each channel's audio signal is then equal to the absolute value or magnitude of the Hilbert transform. FIG. 6 is a graph showing the absolute value or magnitude of the Hilbert transform of the band-pass filtered audio signal shown in FIG. 5. As such, FIG. 6 shows the envelope of the input signal.

Figure 7:
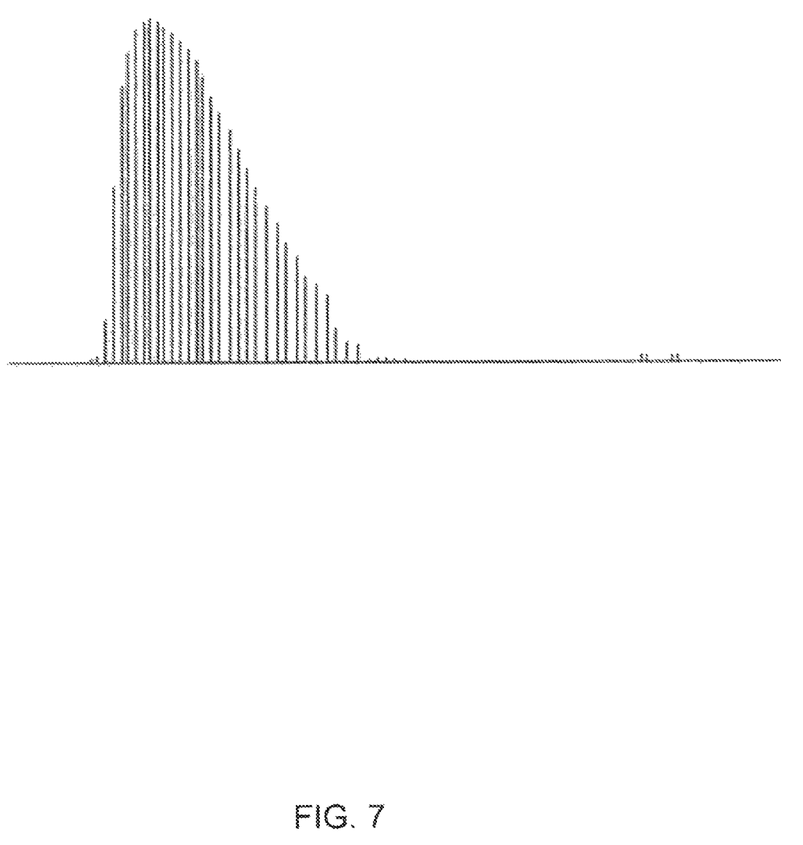
FIG. 7 is a graph showing the stimulating wave formed generated in response to the input audio channel signal shown in FIG. 5 using the Hilbert transform.

Returning to FIG. 3, after generating the Hilbert transform of the input audio signal, in step 310, the sound processor identifies positive-going zero-crossings of the angle of the Hilbert transform. The phase, or angle, of the Hilbert transform is a signal that varies from −pi to pi with the same frequency as the original waveform signal. As such, the angle of the Hilbert transform is representative of the temporal fine structure of the original channel waveform. The positive-going zero-crossings of the Hilbert transform occur at or near the maxima in the input audio signal. In step 312, upon identifying each positive-going zero crossings of the Hilbert transform, the sound processor generates an output of an electric current pulse. It is the combination of these output electric current pulses that become the stimulating control signal for that channel (and corresponding electrode). FIG. 7 is a graph showing the stimulating wave formed generated in response to the input audio channel signal shown in FIG. 5 using the Hilbert transform.

The magnitude of each current pulse in the stimulating control signal can be at least partially determined by the magnitude of the input audio signal when the relevant zero-crossing is detected. In one implementation, the magnitude of each current pulse in the stimulating control signal is equal to the square root of the sum of the squares of the real and imaginary components of the Hilbert transform. Alternatively, the magnitude of each current pulse in the stimulating control signal may be determined by the magnitude of the envelope of the audio signal calculated in step 308 at the time a zero-crossing is detected.

Alternatively, the magnitude of the input audio signal may be used to determine the output magnitude of the stimulating control signal. In that case, sound levels are transformed from sound pressure levels to current levels. The levels can be compressed from the maximum and minimum sound pressure levels in the input waveform to the maximum and minimum current levels via the following equations.

Equation (1) calculates the electric dynamic range (A) from the acoustic dynamic range.

$$A=(MCL-THR)/(HAL\hat{\ }p-LAL\hat{\ }p) \quad \text{Equation (1)}$$

Equation (2) calculates the baseline current (B).

$$B=THR-A*LAL\hat{\ }p \quad \text{Equation (2)}$$

After solving Equations (1) and (2), the electric current level can be calculated according to Equation (3).

$$\text{Electric current level}=A*(\text{acoustic level})\hat{\ }p+B \quad \text{Equation (3)}$$

In Equations (1), (2), and (3), MCL=maximum comfortable level of electric current, THR=threshold of hearing level of electric current, HAL=highest acoustic level, LAL=lowest acoustic level, and p=exponential scaling parameter (in one implementation, set to 2/3).

The stimulating control signal pulses can then be delivered into one or more electrodes disposed within the user's cochlea to stimulate nerves therein to generate the perception of sound.

In some cases, there will be a delay between each actual maxima of the audio signal or the zero-crossing of the Hilbert transform of the input audio signal, and the corresponding stimulating control signal pulse that is ultimately generated by the sound processor and delivered to the cochlear of the user. The delay may be due to the time it takes the sound processor to analyze the incoming audio signal and then generate the output stimulating control signal based upon that input. Delays may also result from resistive-capacitive delays within the cochlear device.

If the pulses of the stimulating control signal are delayed, because the delay of each pulse may be constant, the stimulating control signal will include a number of pulses that are each offset from their target maxima (or Hilbert zero-crossings) in the input audio signal by an equal, fixed amount (e.g., the amount of delay introduced by the circuitry of the cochlear implant device). Because all pulses in the stimulating control signal are similarly offset, the stimulating control signal will include a series of non-periodic pulses that are timed in the same manner as the non-periodic maxima or the zero crossings in the Hilbert angle of the input audio signal. As such, the stimulating control signal, even if offset, provides the benefits as described above.

In the case of a high-frequency input audio signal, the sound processor may be configured to insert a minimum delay between pulses to establish a maximum number of pulses that may be delivered over a particular time period. The minimum delay may result in, for example, a maximum of 2,000 pulses per second being present within the stimulating control signal at a given electrode. In some cases, the minimum delay may be randomized to minimize the potential of adaptation. Minimum and maximum refractory periods are chosen such that after a current pulse has fired on a given electrode, another current pulse is prevented from being generated on that electrode for a period of time whose length is a random value between these minimum and maximum refractory values. Additionally, the sound processor may simply delete or otherwise drop pulses from the stimulating control in order to avoid pulses on different electrodes overlapping in time.

When employing the methods described above (e.g., as illustrated in FIG. 3) for generating a stimulating control signal within a cochlear implant, the resulting control signal includes a train of pulses that are timed to coincide (although each pulse may be delayed by a short time) with the maxima of the input audio signal waveform or the positive zero crossing of the angle of a Hilbert transform of the input audio signal. When the consecutive maxima of zero crossing of the input audio signal are not strictly periodic and, as result, the pulses of the control signal are not strictly period, the negative effects of adaptation are minimized allowing the user of the cochlear implant better use of both monaural and binaural cues.

Additionally, because the control signal generated in response to low-frequency input audio signal includes pulses occurring at a relatively low rate, users of the cochlear implants will have improved rate discrimination allowing for better pitch determination and interaural time difference discrimination for localization ability.

Figure 8:
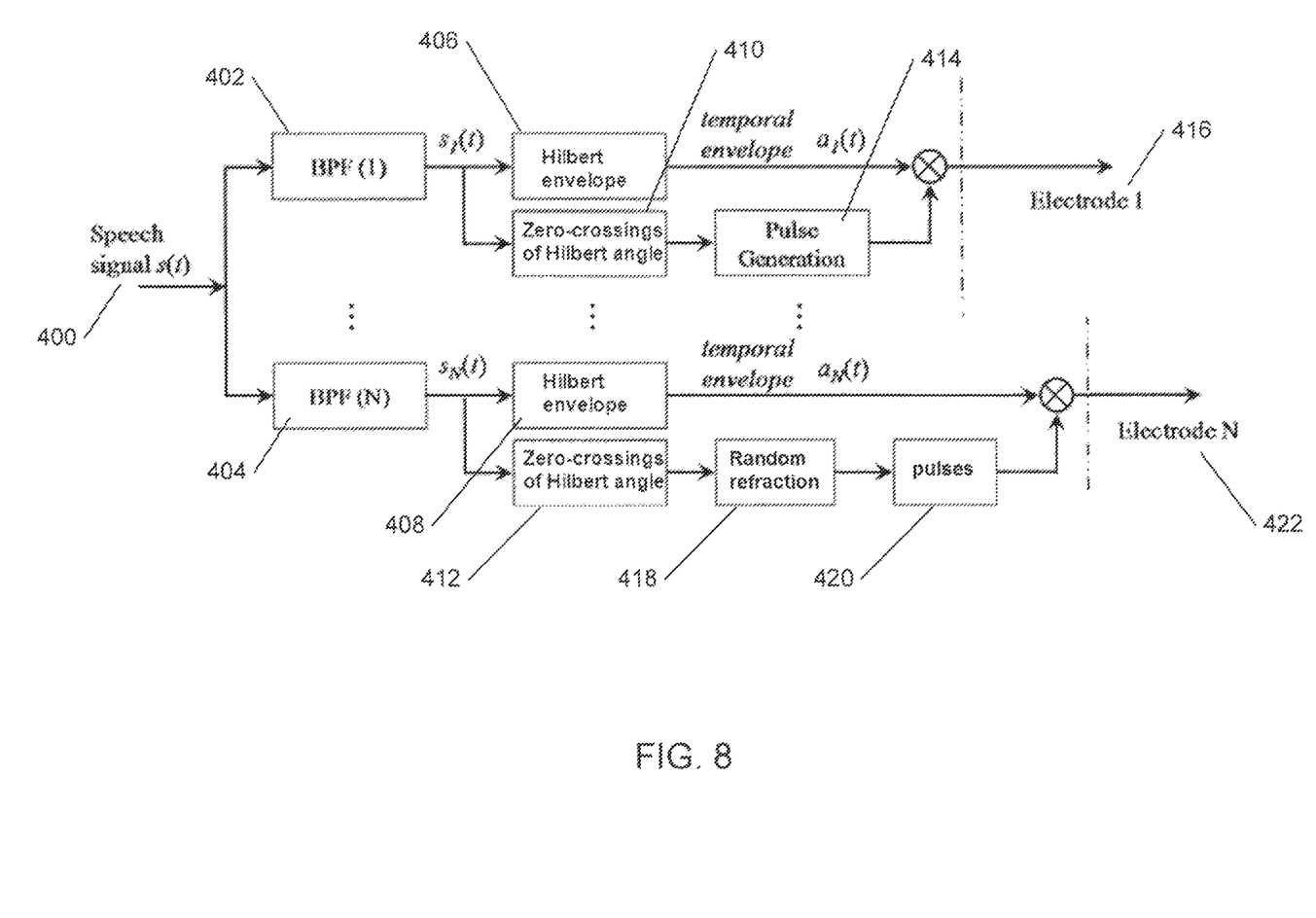
FIG. 8 is a block diagram showing functional components of a system for implementing an algorithm for encoding sound in accordance with the present disclosure.

FIG. 8 is a block diagram showing functional components of a system for implementing an algorithm for encoding sound in accordance with the present disclosure. Referring to FIG. 8, incoming sound signal 400 is band-pass filtered into a number of channels BPF(1) through BPF(N) (402 and 404). After band-pass filtering, the Hilbert envelope (406 and 408) and the Zero-crossing of the Hilbert angle (410 and 412) are calculated for each channel. As shown for channel BPF(1), the zero crossings of the Hilbert angle 410 are used by pulse generation 414 to generate pulses that are ultimately communicated to electrode 416. The magnitude of each pulse is at least partially determined by the magnitude of Hilbert envelope 406 at the time the zero-crossing is detected.

In processing channel 404, the zero-crossings of the Hilbert angle 412 are again used for pulse generation. However, a random refraction 418 is inserted between the detection of the zero crossings and the generation of the pulses 420 to delay one or more of the pulses. The pulses are then ultimately delivered to Electrode N 422, with the magnitude of each pulse being at least partially determined by the magnitude of Hilbert envelope 408 at the time the zero-crossing is detected.

The system and method described above may be embodied in cochlear implant software in the cochlear implant's processor (e.g., the piece that is worn outside the body behind the ear). Alternatively, the methods may be incorporated into assistive listening devices for cochlear implant users, such as CD players or digital media players.

The present system has been described in terms of one or more preferred embodiments, and it should be appreciated that many equivalents, alternatives, variations, and modifications, aside from those expressly stated, are possible and within the scope of the invention.

The invention claimed is:

1. A cochlear implant, comprising:
    an electrode configured to be disposed within a cochlea of a user; and
    a processor in communication with the electrode and configured to stimulate the electrode, the processor being configured to:
        receive an input audio signal,
        band-pass filter the input audio signal into a plurality of channel signals,
        apply a Hilbert transform to at least one of the plurality of channel signals to generate a transformed audio signal,
        analyze the transformed audio signal to identify at least one positive-moving zero crossing of the transformed audio signal, and
        upon identifying the at least one positive-moving zero crossing of the transformed audio signal, trigger an electric current pulse to be delivered to the electrode, wherein the processor is configured to impose a refractory period between electric current pulses, and wherein the refractory period imposed between electric current pulses is randomized to be a value between a minimum refractory period and a maximum refractory period.

2. The cochlear implant of claim 1, wherein a maximum frequency of the electric current pulses is approximately 2,000 pulses per second.

3. The cochlear implant of claim 1, wherein a magnitude of the electric current pulse is at least partially determined by a magnitude of the input audio signal.

4. A method of generating a stimulating signal for a hearing assistance device, comprising:
    receiving an input audio signal,
    band-pass filtering the input audio signal into a plurality of channel signals,
    applying a Hilbert transform to at least one of the plurality of channel signals to generate a transformed audio signal,
    analyzing the transformed audio signal to identify at least one positive-moving zero crossing of the transformed audio signal,
    upon identifying the at least one positive-moving zero crossing of the transformed audio signal, triggering an electric current pulse to be delivered to an electrode; and
    imposing a refractory period between electric current pulses, wherein the refractory period imposed between electric current pulses is randomized to be a value between a minimum refractory period and a maximum refractory period.

5. The method of claim 4, wherein a maximum frequency of the electric current pulses is approximately 2,000 pulses per second.

6. The method of claim 4, wherein a magnitude of the electric current pulse is at least partially determined by a magnitude of the input audio signal.

7. A method of generating a stimulating signal for a cochlear implant, comprising:
    receiving a signal,
    applying a Hilbert transform to the signal to generate a transformed signal,
    analyzing the transformed signal to identify at least one positive-moving zero crossing of the transformed signal,
    upon identifying the at least one positive-moving zero crossing of the transformed signal, triggering an electric current pulse to be delivered to an electrode, and
    imposing a refractory period between electric current pulses, wherein the refractory period imposed between electric current pulses is randomized to be a value between a minimum and a maximum refractory period.

8. The method of claim 7, wherein the maximum frequency is approximately 2,000 pulses per second.

9. The method of claim 7, wherein a magnitude of the electric current pulse is at least partially determined by a magnitude of the input signal.

* * * * *